United States Patent [19]

Pope

[11] Patent Number: 5,606,131
[45] Date of Patent: Feb. 25, 1997

[54] PISTON MANOMETER WITH SPRING CONSTANT DEPENDENT UPON POSITION

[75] Inventor: James W. Pope, North Fort Myers, Fla.

[73] Assignee: Smiths Industries Medical Systems, Inc., Keene, N.H.

[21] Appl. No.: 562,934

[22] Filed: Nov. 27, 1995

[51] Int. Cl.⁶ ................................ G01L 7/16; A61B 5/03
[52] U.S. Cl. ............................................. 73/744; 128/748
[58] Field of Search ......................... 73/744, 745, 746; 128/748, 672, 673, 675

[56] References Cited

U.S. PATENT DOCUMENTS

| | | |
|---|---|---|
| 2,038,928 | 4/1936 | Farley et al. ............................ 73/744 |
| 2,278,776 | 4/1942 | Fowler ................................... 73/744 |
| 3,874,378 | 4/1975 | Isaacson et al. . |
| 3,964,476 | 6/1976 | Palleni . |
| 4,098,271 | 7/1978 | Maddock . |
| 4,106,502 | 8/1978 | Wilson . |
| 4,203,385 | 5/1980 | Mayer et al. . |
| 4,239,038 | 12/1980 | Holmes . |
| 4,249,527 | 2/1981 | Ko et al. . |
| 4,361,107 | 11/1982 | Gereg . |
| 4,374,521 | 2/1983 | Nelson et al. . |
| 4,440,163 | 4/1984 | Spergel . |
| 4,468,969 | 9/1984 | Schwartz . |
| 4,539,985 | 9/1985 | Magrath . |
| 4,584,997 | 4/1986 | Delong . |
| 4,821,713 | 4/1989 | Bauman . |
| 4,945,918 | 8/1990 | Abernathy . |
| 4,966,035 | 10/1990 | Huang ............................... 73/744 X |
| 5,067,487 | 11/1991 | Bauman . |
| 5,076,267 | 11/1991 | Pasternack . |
| 5,109,840 | 5/1992 | Daleiden . |
| 5,140,982 | 8/1992 | Bauman . |
| 5,301,667 | 4/1994 | McGrail et al. . |
| 5,313,938 | 5/1994 | Garfield et al. . |
| 5,334,182 | 8/1994 | Simons et al. . |
| 5,427,091 | 6/1995 | Phillips . |

Primary Examiner—Richard Chilcot
Assistant Examiner—Joseph L. Felber
Attorney, Agent, or Firm—Marshall, O'Toole, Gerstein, Murray & Borun

[57] ABSTRACT

A manometer for use in a patient's breathing circuit, comprising a housing forming a bore and a slider movably mounted within the bore. The slider is movable between an at-rest position, an expanded pressure range, and a contracted pressure range. A spring is connected to the slider for urging the slider toward the at-rest position, while allowing movement of the slider in the two ranges due the pressure in the breathing circuit. The housing is connectable to the breathing circuit such that the gas pressure moves the slider from the at rest position and into at least the expanded pressure range. At relatively low pressures, the slider is moved into the expanded pressure range and at higher pressures, the slider is moved into the contracted pressure range against the force of the spring. The spring is formed by a relatively short tension spring and a relatively long tension spring.

8 Claims, 4 Drawing Sheets

PISTON MANOMETER WITH SPRING CONSTANT DEPENDENT UPON POSITION

FIELD AND BACKGROUND OF THE INVENTION

This invention relates to a manometer for measuring the elastic pressure of gases and/or vapors, and more specifically to a low cost disposable manometer having two pressure ranges or scales.

It is common practice to include a manometer in the breathing circuit of a patient, to display breathing pressure to an attendant. Breathing circuits of this nature include ventilator breathing circuits, resuscitation bags, hyperinflation bags, etc. As an example, U.S. Pat. No. 5,140,982 issued to Jack Bauman on Aug. 25, 1992 shows a resuscitator including a manometer.

Primarily because of the danger of transmission of infectious diseases, it has become common practice in recent years to dispose of breathing circuit components after a single use. There has therefore been an effort to produce disposable components, including manometers, which have a relatively low cost and yet are accurate and dependable.

It is therefore a general object of the present invention to provide an improved disposable manometer for use in a patient's breathing circuit.

SUMMARY OF THE INVENTION

A manometer constructed in accordance with the present invention is for use with a source of gas under pressure, and comprises a housing forming a bore and a float movably mounted within the bore. The float is slidably movable between an at-rest position, an expanded pressure range, and a contracted pressure range. Spring means is connected to the float for urging the float toward the at-rest position while allowing movement of the float in the two ranges due the gas pressure. The housing is connectable to the source of gas such that the gas pressure moves the float from the at rest position and into at least the expanded pressure range. At relatively low pressures, the float is moved into the expanded pressure range and at higher pressures, the float is moved into the contracted pressure range against the forces of the spring means.

BRIEF DESCRIPTION OF THE DRAWINGS

The invention will be better understood from the following detailed description taken in conjunction with the accompanying drawings, wherein.

DETAILED DESCRIPTION OF THE INVENTION

Figure 6:
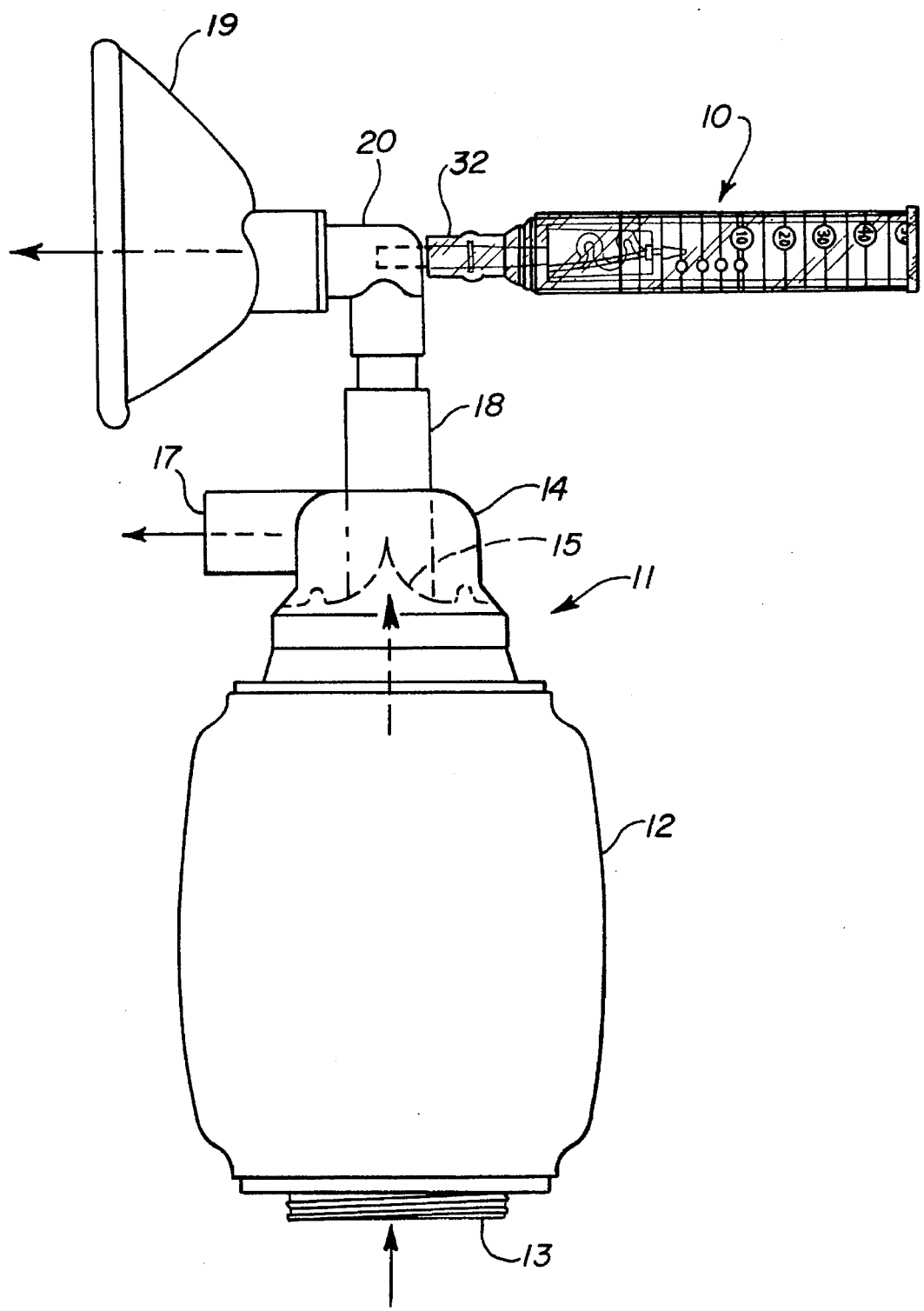
FIG. 6 is a view of a breathing circuit including a manometer in accordance with this invention.

While the manometer may be used in a variety of breathing circuits, FIG. 6 illustrates the manometer 10 in use as part of a disposable manual resuscitator 11. The resuscitator 11 is described in greater detail in W. F. Cook U.S. Pat. No. 4,774,941 dated Oct. 4, 1988, but it should be understood that the manometer 10 may instead be used with other resuscitator designs. Briefly, the resuscitator 11 comprises a squeeze bag 12 having a check valve 13 at its bottom end. At its upper end is fastened a valve housing 14 and a duck-bill valve 15. The housing 14 includes an exhaust port 17 and a tubular air duct 18, and a mask 19 is connected to receive air and/or other gases from the duct 18. In the specific example illustrated in the drawings, the manometer 10 is connected to an adaptor 20 which is between the duct 18 and the mask 19. In use, when an attendant squeezes the bag 12, air is forced from the bag upwardly through the valve 15, the duct 18 and the mask 19 to a patient (not shown). The manometer 10 is connected to the adaptor 18 and shows the air pressure which is being delivered to the patient.

The term "air" is defined herein to include ambient air, gases, vapors and mixtures of such substances.

Figure 1:
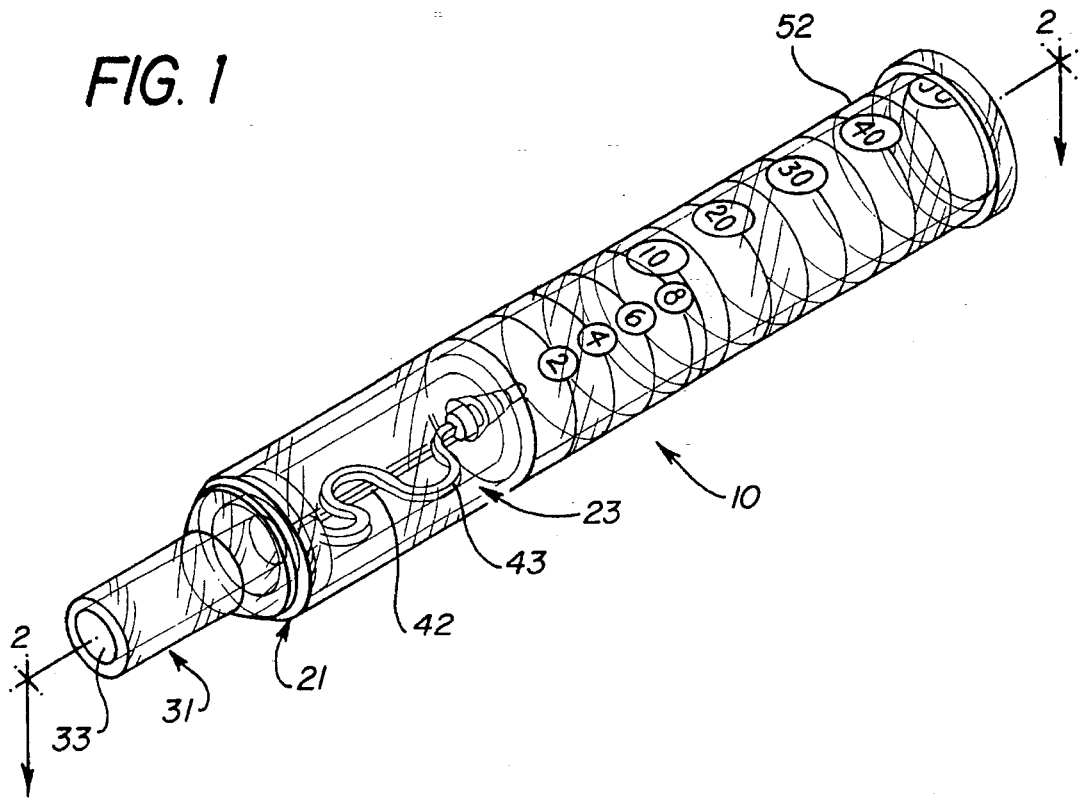
FIG. 1 is a perspective view of the manometer.
Figure 2:
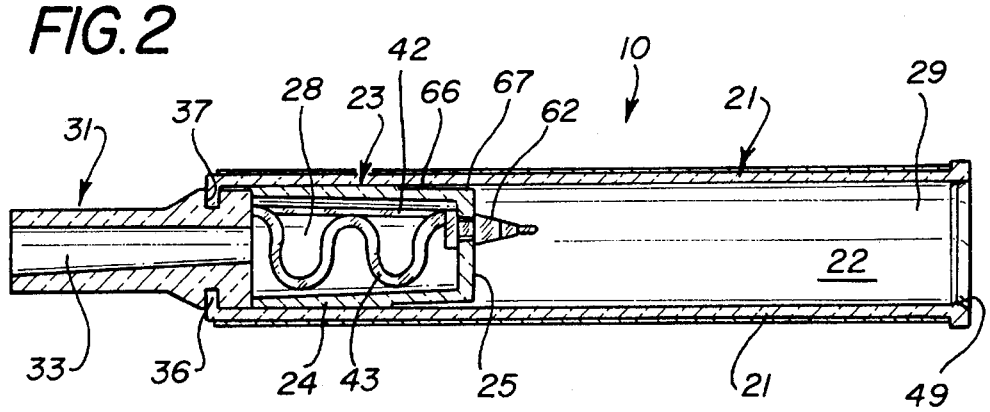
FIG. 2 is a sectional view taken on the line 2—2 of FIG. 1.
Figure 3:
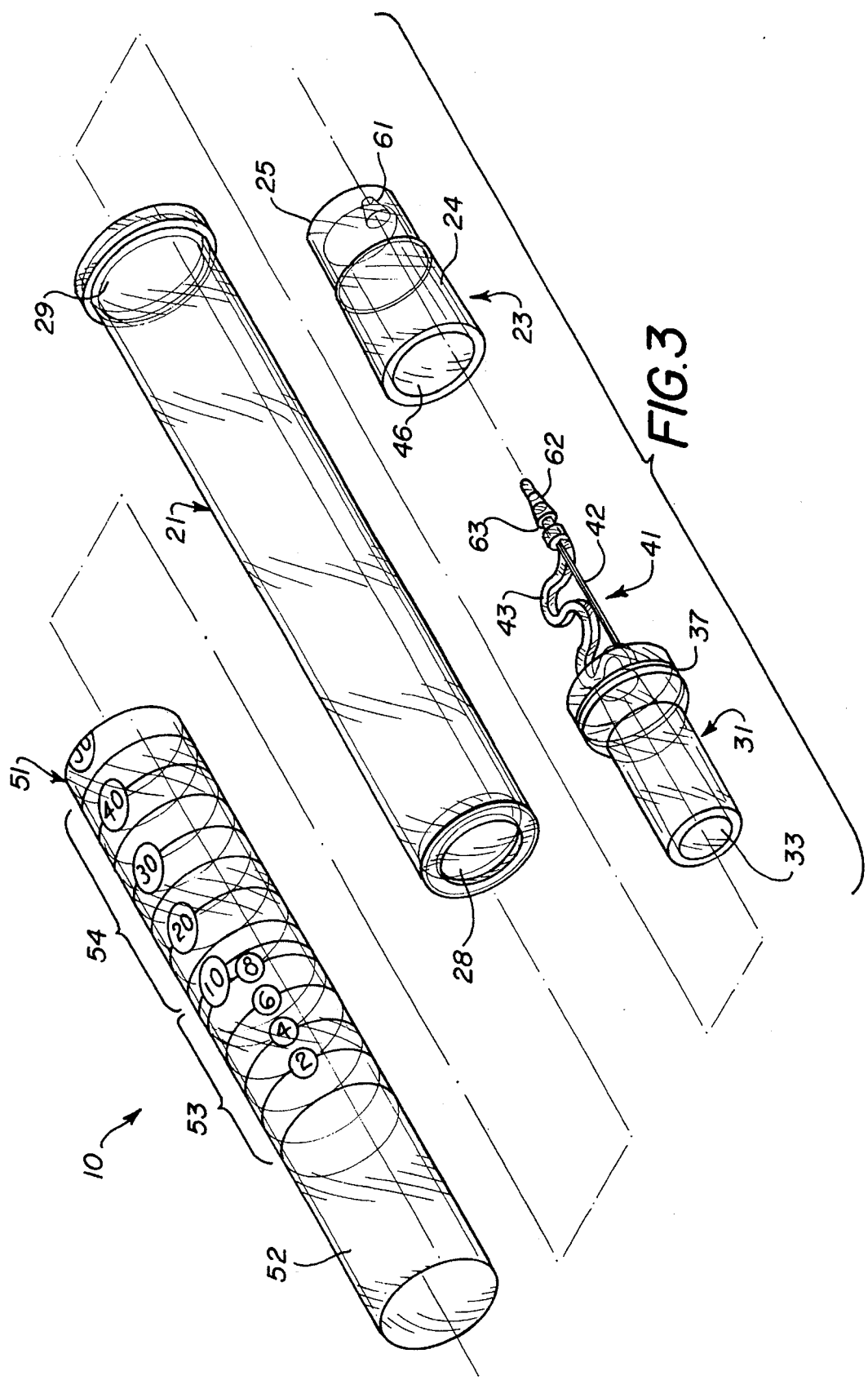
FIG. 3 is an exploded, perspective view of the manometer.

With specific reference to FIGS. 2 and 3, the manometer 10 comprises a tubular housing 21 which forms an internal bore 22, and a slider is movably mounted in the bore 22. While the slider may take various other configurations such as a sphere, in the present specific example of the invention, the slider is in the shape of a piston 23. The piston 23 is formed by a tubular piston skirt 24 and a crown 25.

The bore 22 includes a patient or device pressure end 28 and an outer end 29 which is at reference or ambient air pressure. A connector 31 is attached to the device pressure end 28 and to a tubular nipple 32 which is formed on the adaptor 20. The connector 31 includes a passage 33 which receives the nipple 32. The nipple 32 forms an air passage which opens into the passage 33 of the connector 31, whereby the air pressure within the adaptor 20 and the patient mask 19 is also present in the passage 33 and in the end 28 of the bore 22 (to the left, as seen in FIG. 2, of the piston 23). Consequently, patient air pressure within the adaptor 20, greater than ambient pressure, tends to move the piston 23 toward the right (as seen in FIG. 2) up to the outer end 29.

The housing 21 is secured to the connector 31 by a radially inwardly extending lip or flange 36 formed on the housing 21 at the end 28. An annular groove 37 in the connector 31 receives the lip 36. The housing 21 (and the piston 23) is made of a relatively rigid and transparent material such as rigid PVC, and the connector 31 is preferably made of a relatively soft and pliable material such as silicone. Consequently, the connector 31, during assembly of the parts, may be deformed sufficiently to insert the right-hand end of the connector into the pressure end 28 of the housing bore and to cause the lip 36 to extend into the groove 37.

The piston 23 is resiliently urged toward the pressure end 28 of the housing 21 by elastic spring means 41 which exhibits two levels of tension. The spring means comprises a relatively short elastic spring 42 and a relatively long elastic spring 43. One end of each of the springs 42 and 43 is attached to the crown 25 of the piston 23, and the other end of each of the springs 42 and 43 is attached to the connector 31 and to the housing 21 at the pressure end 28.

Figure 4:
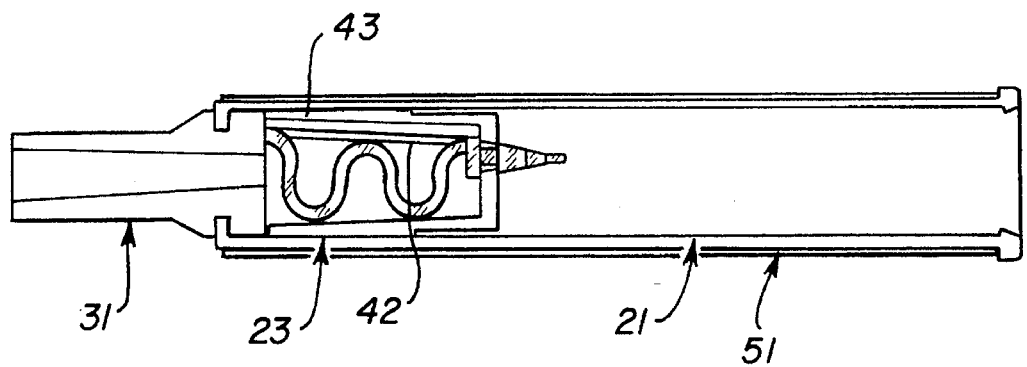
FIG. 4 is a schematic diagram illustrating one position of the parts.

With specific reference to FIG. 3, the skirt 24 and the crown 25 of the piston 23 form a hollow interior 46 which opens toward the pressure end 28 of the housing 21, and the interior 46 forms a chamber for the two springs 42 and 43. The skirt 24 abuts the connector 31 (and thus forms a stop) when the piston 23 is at the pressure end of the housing, and the position of the piston 23 shown in FIG. 2 is referred to herein as the "at rest" position. The piston 23 is urged to the at rest position by the short spring 42, whereas the long spring 43 is not tensioned at this position and is coiled within the chamber 46. The length of the short spring 42 is sized to be under light or no tension when the piston is at the at rest position illustrated in FIGS. 2 and 4.

Figure 5:
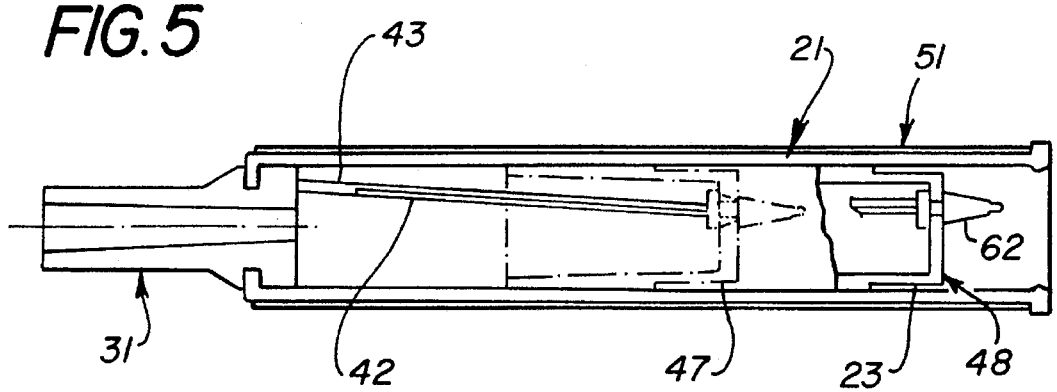
FIG. 5 is a schematic diagram, similar to FIG. 4 but illustrating another position of the parts.

When the pressure delivered to the patient and within the face mask 19 and the adaptor 20 rises above ambient pressure (due to squeezing of the bag 12) the pressure on the left side (as seen in FIG. 2) of the piston 23, which faces the pressure end 28 of the bore, rises above the reference or ambient pressure on the right side of the piston. This rise in patient pressure causes the piston 23 to move toward the right against the tension of the spring 42, with the further result that the long spring 43 unfolds and straightens. The amount of movement of the piston toward the right is proportional to the patient pressure. If the pressure rises sufficiently high, the piston 23 reaches the position shown in dash-dot lines 47 in FIG. 5, at which point the long spring 43 has straightened out. At still higher patient pressures, the piston moves still further toward the right toward the solid line position 48 in FIG. 5, and in this range of movement both springs 42 and 43 exert a tension or force urging the piston toward the at-rest position. Means such as an annular lip 49 is preferably provided to prevent the piston 47 from moving out of the right or low pressure end 29 of the housing 21.

The housing 21 is preferably provided with markings or scale gradations to give a visual indication of the pressure levels associated with the various positions of the piston. While the scale may be marked directly on the housing 21, in the specific example illustrated herein, scale markings 51 are formed on a transparent sleeve 52, and the sleeve 52 fits tightly around the outside of the housing 21 (see FIGS. 2 and 3). As best illustrated in FIG. 3, the markings 51 include an expanded scale range 53 and a compressed scale range 54. Various positions on the piston 23 may be measured against the scale markings, such as the crown 25 of the piston, and the crown may be given a distinguishable or contrasting color to make its position visible.

In the present specific example, the markings in the expanded scale range 53 are adjacent the piston crown 25 while at the at-rest position and during the range of movement when only the short spring 42 is tensioned. The piston crown is adjacent the markings of the compressed scale range 54 when both the short and the long springs are tensioned. When only the short spring is tensioned, a relatively small change of pressure is sufficient to move the piston a given distance; consequently, while the lengths of the two ranges 53 and 54 may be generally similar, the pressure variation over the expanded range 53 is substantially less than the pressure variation over the compressed range 54. In this specific example, the expanded range 53 includes pressure markings indicating 0-2-4-6-8 pressure units above the reference pressure, and the compressed range 54 includes markings indicating 10-20-30-40-50 pressure units. The crown 25 of the piston is at the 0 mark when the piston is at the at-rest position (is against the stop formed by the connecter 31), and is at approximately the 10 mark when the long spring 43 has straightened out and is on the verge of exerting tension on the piston (simultaneously with the short spring 42, of course).

While other constructions may be provided for the springs 42 and 43, such as two coiled metal tension springs, in the present instance, the two springs are formed of an elastic material such as silicone. For example, an elongated band of silicone may be cut lengthwise from one end to nearly the other end to form two strips which are attached at one end, and then one of the two strips may be cut off to a shorter length to form the short spring. Any spring means may be used which provides one tension force over one range of piston movement and another tension force over another range of piston movement. The described arrangement of an expanded scale at lower pressure for convenient readability and a compressed scale at higher pressures where less discrimination is acceptable, is particularly advantageous.

As shown in FIG. 3, one end of each spring 42 and 43 is attached to the connecter 31 and the other end of each spring is attached to the piston 23. In this example of the invention, a hole 61 (FIGS. 2 and 3) is formed through the piston crown 25 and a soft pliable nipple 62 is attached to the right-hand ends of the two springs. The nipple 62 has an annular groove 63 in it, and when the nipple is pressed through the hole 61, the edge of the hole extends into the groove 63 thereby holding the nipple attached to the piston. While the right-hand ends of the springs 42 and 43 may be attached to various locations on the piston, it is preferred that the point of attachment be offset slightly from the axis of the piston as shown in FIG. 2. This arrangement serves to reduce any audible vibration caused by undamped oscillation of the piston, due to the springs 42 and 43 when pressure is applied. As is also illustrated in FIGS. 2 and 3, one of the springs has a greater cross-sectional area than the other spring and therefore has a different spring rate when tensioned.

As best illustrated in FIG. 2, the piston 23 has a slightly reduced outer diameter as indicated by the numeral 66, and a further reduced outer diameter as indicated by the numeral 67, adjacent the crown 25. These portions 66 and 67 reduce the surface contact area between the skirt 24 and the housing 21, and they reduce the likelihood that the piston will become cocked and jammed in the bore 22 due to the tension of the springs.

In one method of assembly of the parts, the connecter 31 and the springs 42 and 43 are secured together and to the nipple 62, and the nipple is attached to the piston 23. Before the lip 49 is formed on the housing 21, the above assembly is inserted into the right-hand end of the bore 22 and the connecter 31 is coupled to the lip 36. The lip 49 is then formed and the sleeve 52 is mounted on the housing 21.

What is claimed is:

1. Apparatus for providing an indication of the magnitude of a device air pressure present in a device relative to a reference air pressure, said apparatus comprising (a) a housing forming an internal bore, said bore having first and second end portions;

(b) said first end portion being connectable to said device such that said device air pressure is present in said first end portion, and said second end portion being exposed to said reference air pressure;

(c) a slider movably mounted in said bore and exposed to said device air pressure, said slider being at an at-rest position when said device air pressure is substantially equal to said reference air pressure; and (d) first and second tension springs connected between said slider and said housing, each of said springs having one end thereof connected to said slider and another end thereof connected to said housing, said slider being movable in two ranges of movement, said first range being adjacent said at-rest position and said second range being displaced from said at-rest position, only said first spring restraining movement of said piston in said first range and both said first and second springs restraining movement of said piston in said second range.

2. Apparatus as set forth in claim 1, wherein said second spring is longer than said first spring.

3. Apparatus as set forth in claim 1, wherein each of said first and second tension springs comprises a stretchable elastic band.

4. Apparatus as set forth in claim 1, wherein said slider comprises a tubular skirt portion and a crown portion, and said first and second springs extend through said skirt portion and are attached to said crown.

5. Apparatus as set forth in claim 4, wherein said crown portion is substantially circular, and said spring means is attached to said crown portion at a point which is displaced from the center of said crown portion.

6. A breathing circuit connectable to a patient and displaying patient breathing pressure, comprising
 (a) a gas conduit connectable to the patient's breathing system;
 (b) a housing forming an internal bore, said bore having first and second end portions;
 (c) said first end portion being connectable to said gas conduit such that said patient breathing pressure is present in said first end portion, and said second end portion being exposed to ambient air pressure;
 (d) a slider movably mounted in said bore and exposed to said patient breathing pressure, said slider being at an at-rest position when said patient breathing pressure is substantially equal to said ambient air pressure; and
 (e) first and second tension springs connected between said slider and said housing, each of said springs having one end thereof connected to said slider and another end thereof connected to said housing, said slider being movable in two ranges of movement, said first range being adjacent said at-rest position and said second range being displaced from said at-rest position, only said first spring restraining movement of said piston in said first range and both said first and second springs restraining movement of said piston in said second range.

7. A breathing circuit as set forth in claim 6, wherein said first and second springs comprise two elastic bands.

8. A breathing circuit as set forth in claim 6, wherein said housing comprises a relatively transparent tubular member forming said bore, and further comprising a tubular connector attached to said housing and extending into said first end portion of said bore.

\* \* \* \* \*